United States Patent [19]
DeMichele et al.

[11] Patent Number: 6,013,665
[45] Date of Patent: Jan. 11, 2000

[54] METHOD FOR ENHANCING THE ABSORPTION AND TRANSPORT OF LIPID SOLUBLE COMPOUNDS USING STRUCTURED GLYCERIDES

[75] Inventors: Stephen J. DeMichele, Dublin; Theresa W. Lee, Upper Arlington; Patrick Tso, Cincinnati, all of Ohio

[73] Assignee: Abbott Laboratories, Abbott Park, Ill.

[21] Appl. No.: 08/991,503

[22] Filed: Dec. 16, 1997

[51] Int. Cl.$^7$ .................. A61K 31/355; A61K 31/07; A61K 47/00
[52] U.S. Cl. ............... 514/458; 514/725; 514/786; 514/946
[58] Field of Search ................. 514/458, 725, 514/786, 946

[56] References Cited

U.S. PATENT DOCUMENTS

| | | | |
|---|---|---|---|
| 4,753,963 | 6/1988 | Jandacek et al. | 514/552 |
| 4,871,768 | 10/1989 | Bistrian et al. | 514/547 |
| 5,081,105 | 1/1992 | Bistrian | 514/2 |

FOREIGN PATENT DOCUMENTS

| | | |
|---|---|---|
| 0 347 843 A1 | 12/1989 | European Pat. Off. . |
| 0 609 001 A2 | 8/1994 | European Pat. Off. . |
| 0 682 879 | 11/1995 | European Pat. Off. . |
| WO 86 01715 | 3/1986 | WIPO . |
| WO 92/19237 | 11/1992 | WIPO . |
| WO 94/15464 | 7/1994 | WIPO . |
| WO 95/31110 | 11/1995 | WIPO . |
| WO 97 39749 | 10/1997 | WIPO . |

OTHER PUBLICATIONS

Fukui, et al., "Enhancing Effect of Medium–Chain Tryglycerides on Intestinal Absorption of d–α–Tocopherol Acetate from Lecithin–Dispersed Preparations in the Rat," *J. Pharmacobio–Dyn.*, 12, 80–86 (1989).

Kimura, et al., "Enhancement of Oral Bioavailability of d–$_x$–Tocopherol Acetate by Lecithin–Dispersed Aqueous Preparation Containing Medium–Chain Triglycerides in Rats," *Chem. Pharm. Bull.* 37(2)439–441 (1989).

Fukui, et al., "Further Investigations of Enhancing Effect of Medium–Chain Triglycerides on d–α–Tocopherol Acetate from Lecithin–Dispersed Preparations in the Rat Small Intestine," *J. Pharmacobio–Dyn.* 12, 754–761 (1989).

Fujimoto, et al., "Effect of ischemia–reperfusion on lipid digestion and absorption in rate intestine," The American Physiological Society, 260 G595–G602 (1991).

Muralidhara, et al., "Intestinal absorption of α–Tocopherol in the unanesthetized rat. The influence of luminal constituents on the absorptive process," *J. Lab. Clin. Med.*, 90, 85–91 (1977).

MacMahon, et al., "Comparison of the Absorption of a Polar Lipid, Oleic Acid, and a Non–Polar Lipid, α–Tocopherol from Mixed Micellar Solutions and Emulsions," Europ. J. Clin. Invest. 1, 161–166 (1970).

Tso, et al., "The Absorption of Lipid and Lipoprotein Synthesis," Lipid Research Methodology, 191–216 (1984).

Chen, et al., "Absorption of Tocopherol in Intestinal Lymph Fistula Rats: Effects of Triolein and Phosphatidylcholine," *Gastroenterology*, vol. 108, No. 4, 1995 (Abstract).

Karleskind, et al., "Oils and Fats Manual, A Comprehensive Treatise", *Transformation of Fat for Use in Food Products*, vol. 2, Chapter 11, pp. 923–925. (1996).

*Primary Examiner*—Kimberly Jordan
*Attorney, Agent, or Firm*—J. Michael Dixon; Thomas D. Brainford

[57] ABSTRACT

This invention relates to a method for enhancing the absorption of oil soluble (lipophilic) compounds such as oil soluble vitamins, hormones, nutrients and drugs in an animal. The inventive method comprises administering a lipophilic compound in conjunction with a structured glyceride component characterized in that at least 40% of the glyceride species have: (i) about 33 to 70 wt. % of acyl moieties having 4 to 12 carbon atoms; (ii) about 30 to 67 wt. % of acyl moieties having more than 12 carbon atoms; and (iii) an equivalent carbon number greater than 30 and less than 48. This invention also relates to compositions suitable for administrating to an animal comprising a lipophilic compound and a structured glyceride component characterized in that at least 40% of the glyceride species have: (i) about 33 to 70 wt. % of acyl moieties having 4 to 12 carbon atoms; (ii) about 30 to 67 wt. % of acyl moieties having more than 12 carbon atoms; and (iii) an equivalent carbon number greater than 30 and less than 48. The method and compositions of the invention are especially suited for animals that suffer from lipid malabsorption conditions such as Crohn's disease, Cystic fibrosis, and short bowel syndrome.

47 Claims, 5 Drawing Sheets

METHOD FOR ENHANCING THE ABSORPTION AND TRANSPORT OF LIPID SOLUBLE COMPOUNDS USING STRUCTURED GLYCERIDES

This invention relates to a method for enhancing the absorption and transport of lipid soluble compounds such as certain vitamins, nutrients and drugs in an animal. The inventive method comprises the administration of one or more lipid soluble compounds in conjunction with a structured glyceride component containing at least 33 wt. % of a fatty acid moiety having 4 to 12 carbon atoms, at least 30 wt. % of a fatty acid moiety having more than 12 carbon atoms and an equivalent carbon number (ECN) greater than 30 to less than 48. This invention also relates to compositions comprising a structured glyceride component and one or more lipid soluble compounds. The most preferred compositions for use in this invention are suitable for enteral administration to an animal.

BACKGROUND

Lipoidal preparations have been extensively studied in an effort to improve drug absorption from the gastrointestinal tract. Mammals with lipid (fat) malabsorption diseases such as Cystic fibrosis, Crohn's disease, Short bowel syndrome and the like, present special problems for the digestion, absorption and lymphatic transport of dietary fat and lipophilic compounds, such as drugs, hormones, nutrients and vitamins since the underlying disease limits the absorption and transport of the lipophilic compound from the gut. Absorption of lipophilic compounds is thus impaired in diseases that cause fat malabsorption.

The development of special dosage forms and the use of various absorption promoters for lipophilic compounds have been extensively studied. For example, Hansen et al. in WO92/109237 disclose the use of specific triglycerides in an enteral preparation for the treatment of lipid malabsorption. This reference specifically discloses the use of a purified lipid having a medium chain acyl moiety at the sn-1 and sn-3 positions and a long chain acyl moiety at the sn-2 position.

U.S. Pat. No. 4,753,963 to Jandacek et al. discloses a nutritional fat suitable for enteral and parenteral products. This patent claims a triglyceride having an N-octanoyl acyl radical or moiety at the sn-1 and sn-3 positions. The sn-2 acyl radical comprises saturated acyl groups selected from the group consisting of N-heptanoyl, N-octanoyl, N-nonanoyl, N-decanoyl, N-undecanoyl, lauroyl, myristoyl, palmitoyl, and stearoyl. This reference also discloses the use of these fats in enteral products comprising carbohydrates, a source of amino acids and optionally, components such as vitamins and minerals.

DeMichele et al. in U.S. Pat. No. 5,661,180 discloses a structured lipid containing a gamma-linolenic acid or a dihomogamma-linolenic acid moiety together with an n-3 fatty acid residue and a medium chain fatty acid moiety. The DeMichele structured lipid is disclosed as being well adapted to the treatment of disease or stress states. This reference also teaches the use of the specific structured lipid to modulate metabolic response associated with trauma and inflammatory disease states.

U.S. Pat. No. 4,871,768 to Bistrian et al. discloses a structured lipid comprising n-3 fatty acid moieties and medium chain fatty acid moieties. More specifically, this patent discloses a synthetic triglyceride comprising a glycerol backbone having three fatty acids esterfied thereto wherein the fatty acids are selected from a first group consisting of n-3 fatty acids and a second group consisting of caprylic acid, capric acid and mixtures thereof. This patent discloses the structured lipids as a dietary supplement for enhancing resistance to infection while providing good nutrition and an excellent source of energy. This reference, like those above, is directed to the use of structured lipids for nutritional value.

International Publication No. WO95/31110 to Lien et al. discloses a co-randomized fat composition for use in nutritional products for pre-term and low birth weight infants. This reference discloses the co-randomization of oils such as palmitic acid oil and an oleic acid oil to yield a mixture of triglycerides having a substantially different chemical profile than that of the starting materials. This reference discloses the use of these specific structured lipids in enteral or parenteral products for infants to approach the fatty acid profile of human milk.

European Patent Application No. 0 347 843 to Tsushima et al. discloses the improved absorption of vitamin E by the digestive system through the use of lecithin and a free unsaturated fatty acid. This reference discloses the free unsaturated fatty acid as preferably being oleic acid or linoleic acid. This reference teaches improved absorption of vitamin E through the combined administration of vitamin E with lecithin (phosphatidylcholine derived from egg yolk or soy beans) in combination with a free unsaturated fatty acid such as linoleic acid or oleic acid.

Kimura et al. in *Chem Pharm. Bull.*, 37(2) 439–441 (1989) entitled, "Enhancement of Oral Bioavailability of d-α-Tocopherol Acetate by Lecithin-Dispersed Aqueous Preparation Containing Medium-Chain Triglycerides in Rats" reports the use of vitamin E/lecithin-dispersed aqueous preparations which increase the lymphatic absorption of vitamin E. This reference also investigated the use of polysorbate 80-solubilized aqueous emulsions of vitamin E and its absorption through the intestinal mucosa. These investigators found that the administration of MCT significantly enhanced the absorption of lecithin-dispersed aqueous preparations of vitamin E by the gastrointestinal tract. It is well established that the absorption of MCT occurs mainly via the portal circulation and not via the lymphatic route. In contrast, vitamin E is transported predominantly via the lymphatic system. It appears from this reference that the mechanism of absorption of vitamin E does not resemble the intestinal transport of MCT.

Two publications by Fukui et al., *J. Pharmacobio-Dyn.*, 12, 80–86 (1989) and *J. Pharmacobio-Dyn.*, 12, 754–761 (1989) report the enhancing effect of MCT on intestinal absorption of vitamin E as does the Kimura et al. reference above. These two references also support the conclusion that MCT absorption and vitamin E absorption use unrelated pathways.

Chen et al. report in "Absorption of Tocopherol in Intestinal Lymph Fistula Rat: Effects of Triolein and Phosphatidylcholine" *Gastroenterology* 108:A720, (1995), that the absorption of vitamin E is influenced by the presence of triolein (triglyceride) and phosphatidylcholine (lecithin). The use of lecithin promotes the water miscibility of the vitamin E. When the same amount of fatty acid was infused in the form of triolein or phosphatidylcholine with vitamin E, the amount of lipid transported to the lymph was similar. In contrast, the transport of vitamin E into lymph was significantly reduced in the animals infused with phosphatidylcholine as compared to those infused with the triglyceride. It thus appears from this work that it is not possible to predict the level of absorption of vitamin E based on the efficiency of triglyceride absorption.

The inclusion of polyunsaturated fatty acids in bile salt micelles is reported to depress α-tocopherol absorption by the rat small intestine. See Muralidhara et al., "Intestinal Absorption of α-Tocopherol in the Unanesthetized Rat. The Influence of Luminal Constituents on the Absorptive Process." *J. Lab. Clin. Med.,* 90:85–91, (1977). It is known that polyunsaturated fatty acids are well absorbed by the gastrointestinal tract. However, Muralidhara et al. demonstrates that the absorption of vitamin E is suppressed by the presence of polyunsaturated fatty acids. The experiments indicate that micellar expansion with polyunsaturated fatty acids interferes with the absorption of tocopherol and may result in deficiency of the vitamin. This reference also supports the belief that better triglyceride absorption is not always associated with enhanced absorption of fat soluble vitamins.

MacMahon et al. have demonstrated in rats with bile diversion that a polar lipid such as oleic acid, is well absorbed into the lymphatic system from an emulsion (from bile salt micelles) while the non-polar α-tocopherol was poorly absorbed from the emulsion. See MacMahon et al. "Comparison of the Absorption of a Polar Lipid, Oleic Acid, and a Non-Polar Lipid, α-Tocopherol from Mixed Micellar Solutions and Emulsions", *European Journal of Clinical Investigation* 1:160–166, 1970. This publication also supports the position that good triglyceride absorption, from an emulsion, is not always associated with good vitamin absorption.

Figure 1:
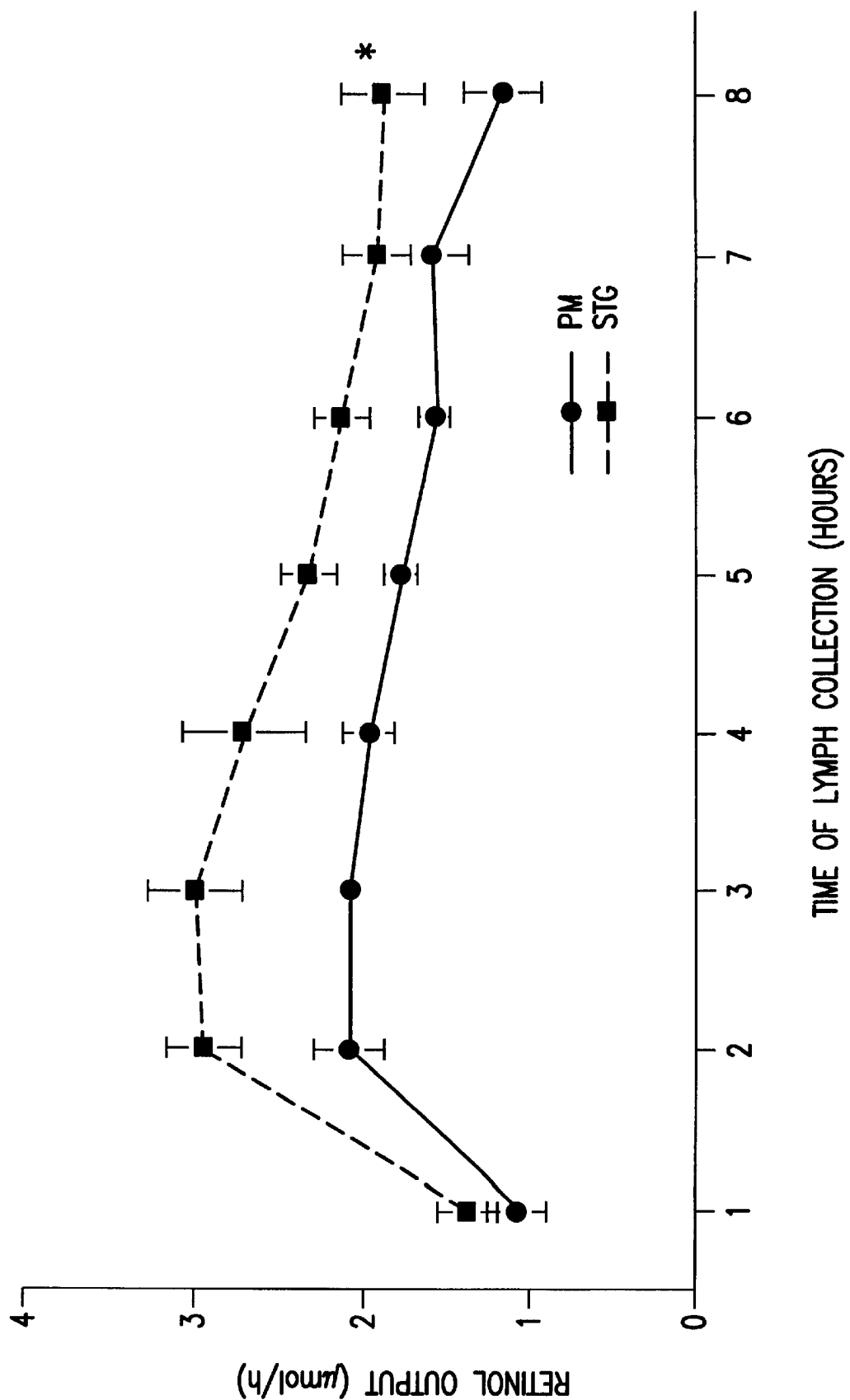
FIG. 1 is a graphic representation of lymphatic retinol absorption for the non-injury model experiment conducted in Example 2.
Figure 2:
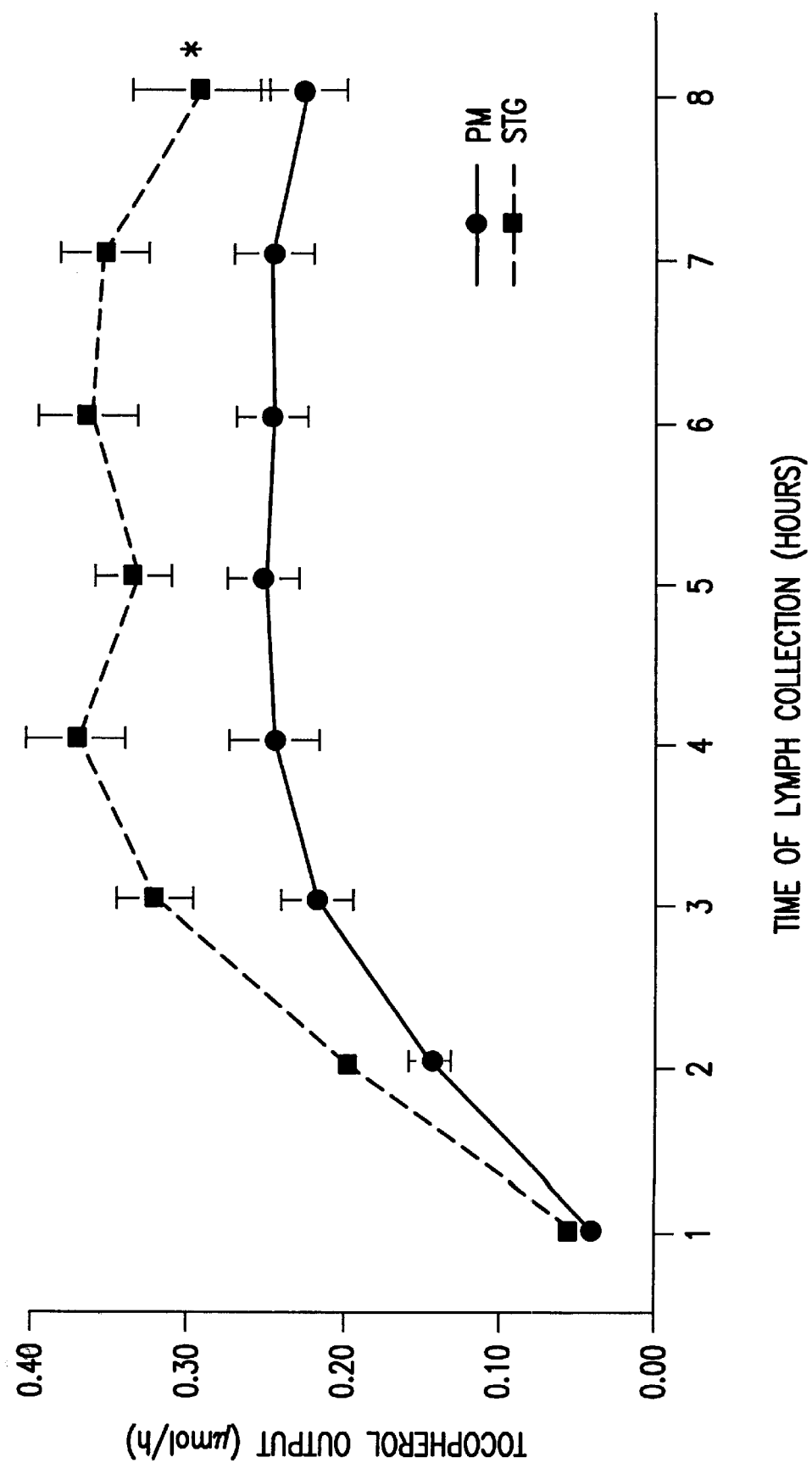
FIG. 2 is a graphic representation of lymphatic tocopherol absorption for the non-injury model experiment conducted in Example 2.

The results set forth in FIGS. 1–4 are statistically significant at $p<0.01$ (see *). A two way analysis of variance model was employed for each treatment, lipid type and their interaction effects in the model were used to compare the area under each curve. Models were extended to included contrast statements comparing the physical mix and the structured triglyceride within each treatment group.

SUMMARY OF THE INVENTION

The present invention has many aspects. In one broad aspect, the invention relates to the discovery that, compared to conventional oils or their physical mixtures, structured glycerides containing at least 33 wt. % of acyl moieties having 4 to 12 carbon atoms, at least 30 wt. % of acyl moieties having more than 12 carbon atoms and an equivalent carbon number ("ECN") ranging from greater than 30 to less than 48 will greatly facilitate the absorption of lipophilic compounds such as fat soluble vitamins, nutrients and drugs. Thus, the invention provides a method for enhancing the absorption of lipophilic compounds in an animal, said method comprises administering to said animal:

a) at least one lipophilic compound in conjunction with
b) a structured glyceride component containing at least 33 wt. % acyl moieties having 4 to 12 carbon atoms, at least 30 wt. % of a acyl moieties having more than 12 carbon atoms and an equivalent carbon number (ECN) of greater than 30 to less than 48.

The structured glyceride component typically includes triglycerides. A structured triglyceride useful in this invention comprises 33 to 70 wt. % acyl moieties of medium chain length (i.e. 4 to 12 carbon atoms). More preferably the medium acyl chains comprise 45 to 70 wt. %, most preferably 50 to 65 wt. %. At all weight percents, the length of the medium acyl chains is preferably 4 to 12 carbon atoms, more preferably 6 to 12, most preferably 8 to 10 carbon atoms. The 30 to 67 wt. % remainder of the structured triglyceride is typically a long chain (13–22 carbon atoms) acyl moiety. More preferably the long acyl chains comprise 30 to 55 wt. %, most preferably 35 to 50 wt. %. Preferably, said long chain acyl moiety at all weight percents comprises a long chain polyunsaturated fatty acid residue. The structured glyceride component is preferably characterized as comprising at least 40% of a species with equivalent carbon number (ECN) of greater than 30 to less than 48, more preferably ECN of about 32 to about 42.

The lipophilic compounds of this invention may be selected from oil soluble drugs, nutrients and vitamins.

The invention further provides a composition suitable for administration to an animal comprising:

a) at least one lipophilic compound and
b) a structured glyceride component containing at least 33 wt. % acyl moieties having 4 to 12 carbon atoms, at least 30 wt. % of a acyl moieties having more than 12 carbon atoms and an equivalent carbon number (ECN) of greater than 30 to less than 48.

In a further aspect, the improved method is useful in an animal that suffers from lipid malabsorption. In such a case, the composition preferably comprises at least one lipophilic compound and a structured glyceride component, said structured glyceride component comprising at least 33 wt. % acyl moieties of 4 to 12 carbon atoms; at least 30 wt. % long chain polyunsaturated acyl moieties and an equivalent carbon number (ECN) of greater than 30 to less than 48.

Other aspects of the invention are described throughout the application.

DETAILED DESCRIPTION

General Terminology

According to this invention, lipophilic compounds are used in conjunction with a structured glyceride component. By "In conjunction with" we mean that the lipophilic compounds are administered to said animal within one hour of administration of the structured glyceride component. More preferably, the lipophilic compounds are administered at the same time as the structured glyceride component, most preferably admixed in the same composition, such as enteral nutritionals, nutritional supplements, tablets, pills, capsules, suppositories, sprays, lozenges, drops, lotions, ointments, microcapsules and liposomes.

The term "lipid" generally denotes a heterogeneous group of substances associated with living systems which have the common property of being insoluble in water, can be extracted from cells by organic solvents of low polarity such as chloroform and ether. The terms "lipophilic compound" and "lipid soluble compound" thus refers to those compounds that have greater solubility in organic solvents such as ethanol, methanol, ethyl ether, acetone, chloroform and benzene and fats and oils than in water. Specific compound solubility is listed in references such as Section C of the CRC Handbook of Chemistry and Physics, 67th Edition, CRC Press and the Merck Index. Lipid soluble compounds include drugs, hormones, vitamins, nutrients and other selected lipophillic compounds, as described in detail later.

The term "structured lipid" generally refers to an oil or fat that contains specific fatty acyl residues in a specific position on the glycerol backbone. As used in this invention, a "structured glyceride component" refers to a glyceride mixture characterized in that it may contain mono-, di- and triglycerides, more typically di- and triglycerides, ideally a higher percentage of triglycerides. At least 40% of the triglyceride species have about 33 to 70 wt. % of acyl moieties having 4 to 12 carbon atoms; about 30 to 67 wt. % of acyl moieties having more than 12 carbon atoms and an equivalent carbon number of greater than 30 to less than 48.

A glyceride is an ester of glycerol (1,2,3-propanetriol) with acyl radicals of fatty acids and is also known as an acylglycerol. If only one position of the glycerol molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. A glyceride is called "simple" if all esterified positions contain the same fatty acid; or "mixed" if different fatty acids are involved. The carbons of the glycerol backbone are designated sn-1, sn-2 and sn-3, with sn-2 being in the middle and sn-1 and sn-3 being the ends of the glycerol.

Naturally occurring oils and fats consist largely of triglycerides wherein the 3 fatty acyl residues may or may not be identical. The term "long chain triglycerides (LCT)" means both a simple and mixed triglyceride containing fatty acids with more than 12 carbon atoms (long chain fatty acids—"LCFA"), whereas the term "medium chain triglycerides (MCT)" means both a simple and mixed triglyceride containing fatty acids with 4 to 12 carbon atoms.

The term "ECN" or "equivalent carbon number" means the sum of the number of carbon atoms in the acyl chains of a glyceride molecule. For example, tripalmitin (tripalmitic glycerol), which is a simple triglyceride containing 3 acyl radicals of 16 carbon atoms, has an ECN of 3×16=48. Conversely, a triglyceride with an ECN=40 may have "mixed" acyl chain lengths of 8, 16 and 16; 10, 14 and 16; 8, 14 and 18, etc. Naturally occurring oils are frequently "mixed" with respect to specific fatty acids, but tend not to contain LCFAs and MCFAs on the same glycerol backbone. Thus, triacylglycerols with ECN's of 24–30 typically contain predominately medium chain fatty acids; while triacylglycerols with ECN's of greater than 43 typically contain predominantly long chain fatty acids. Triacylglycerols having an ECN's of 32–42 typically contain one or two MCFA in combination with one or two LCFA's to "fill" the triglyceride. Triacylglycerols with ECN's in the range of greater than 30 to less than 48 typically represent mixed triacylglycerol species that are essentially unique to the structured triglyceride and are absent from or are present in significantly lower concentrations in physical mixtures.

Many of the properties of food lipids can be accounted for directly in terms of their component fatty acids. The fatty acids that occur in foodstuffs usually contain an even number of carbon atoms in an unbranched chain, e.g., lauric or dodecanoic acid. Besides the saturated fatty acids, of which lauric acid is an example, fatty acids may have 1, 2 or sometimes up to 6 double bonds and are, therefore, unsaturated. The number and position of double bonds in fatty acids are designated by a convention of nomenclature typically understood by the organic chemist. For example, arachidonic acid ("AA" or "ARA") has a chain length of 20 carbons and 4 double bonds beginning at the sixth carbon from the methyl end. As a result, it is referred to as "20:4 n-6". Similarly, docosahexaenoic acid ("DHA") has a chain length of 22 carbons with 6 double bonds beginning with the third carbon from the methyl end and is thus designated "22:6 n-3".

The terms "wt. %" or "weight percent" means the ratio of the mass of the recited component to the mass of the specified ingredient or entire composition multiplied by 100. For example, "a triglyceride comprising 40 wt. % acyl moieties of 10 carbon atoms" means that 100 gms of the triglyceride oil consists of 40 gms of 10 carbon atoms acyl radicals and 60 gms of other components, including other acyl radicals and the glycerol backbone.

The term "fish oil" means the oil derived from fish sources, such as menhaden, sardine, cod and the like. Fish oil has gained much attention in recent years as Eskimos, who consume high levels of fish oils, have a remarkably low incidence of arterial disease. Fish oils are rich in polyunsaturated long chain fatty acids such as eicosapentaenoic acid (20:5n-3) and docosahexaenoic acid (22:6n-3).

Compositions

The compositions useful in the method of enhancing the absorption and transport of lipophilic compounds comprise a structured glyceride component of at least 33 wt. % randomly esterified MCFA. The remainder of the fatty acid moieties are typically LCFA. The source of the MCT and LCT to prepare the structured glyceride component is not critical. Typical sources of MCT such as fractionated coconut oil and fractionated palm kernel oils are known to those skilled in the art. Sources of LCFA include the oils derived from borage, black currant seed, corn, coconut, canola, soybean, marine oils, fungal oils, safflower, high oleic safflower, sunflower, high oleic sunflower, olive, evening primrose, cottonseed, rice bran, grapeseed, flaxseed, butterfat, garlic, peanuts, almonds, walnuts, wheat germ, egg, sesame, lard, tallow and mutton.

In a more preferred embodiment, the structured glyceride of the invention also contains a long chain polyunsaturated fatty acid (hereinafter "LCPUFA") such as the n-6, n-9 and/or n-3 long chain fatty acids. Known sources of LCPUFA include fish or marine oil, egg yolk lipid, single cell oils (e.g., algal oils and fungal oils), it being understood in the art that some sources are better than others for achieving higher amounts of a specific LCPUFA. Other edible, semi-purified or purified sources of LCPUFA will be evident to persons skilled in the art. For example, new sources of LCPUFAs may be developed through the genetic manipulation of vegetables and oil bearing plants. The use of such recombinant oils are also contemplated in the present invention.

The structured glycerides useful in the present invention contain both MCFA and LCFA. The structured tryglycerides useful in this invention are chemically distinct and offer unique advantages from the starting materials from which they are derived. One aspect of the present invention resides in the discovery that structured triglycerides that contain a certain mixture of MCFA and LCFA are subject to rapid hydrolysis and absorption in comparison to LCT's. In addition, the structured triglycerides of this invention are primarily absorbed and transported through the lymphatic system as opposed to the hepatic route.

In native fats and oils, the various fatty acids are esterified through one of the three hydroxy groups of the glycerol molecule in an ordered pattern that is characteristic of the particular fat or oil. In general, the naturally occurring, long chain, saturated fatty acids (e.g., $C_{16}$–$C_{18}$) are predominantly at the sn-1 and sn-3 positions, while the mono- and polyunsaturated fatty acids are at the sn-2 or middle position of the triglyceride molecule. There are only a small number of naturally-occurring "simple triglycerides", for example, tripalmitin ($C_{16}$), triolein ($C_{18}$) and the like.

The structured glyceride component of this invention will predominantly contain triglycerides, 50% by weight or more, frequently about 90% by weight. Of these triglycerides (whatever their proportion) at least 40% by weight have an ECN greater than 30 and less than 48. More preferably, the structured glyceride component will contain at least 60% by weight the ECN greater than 30 and less than 48 species, most preferably at least 60% by weight the ECN of about 32 to about 42 species.

Utility

A further aspect of the present invention resides in the discovery that a structured glyceride according to the invention can act as a carrier to facilitate the delivery (absorption) of fat soluble vitamins (e.g. A, E, D, K and carotenes) as well as other lipophilic natural and synthetic drugs. While there may exist some evidence that the use of MCT or LCT oils alone may enhance the absorption of tocopherol, the state of the art is at best unable to predict with any level of certainty which oils and which compounds will evidence enhanced lymphatic absorption. There is no suggestion or disclosure in the prior art that a particular structured triglyceride would enhance the lymphatic absorption and transport of lipophilic compounds in healthy animals or in animals with lipid malabsorption. Further, the prior art teaches that the absorption mechanisms of fat soluble vitamins do not resemble the absorption of dietary triglycerides. Thus, this invention is based, in part, on the discovery that a certain class of structured glyceride will significantly improve the absorption of the lipophilic compound into the lymphatic system. This invention is an especially meaningful discovery since patients with malabsorption diseases such as Crohn's disease are at increased risk of developing vitamin E, A and/or D deficiencies and these patients also present special problems in the delivery of lipophilic drugs.

The lipophilic compounds of this invention may be selected from oil soluble drugs, nutrients and vitamins. Representative of the oil soluble drugs useful in the present invention are the natural and synthetic forms of immunosuppressive agents such as Cyclosporin™, protease inhibitors such as Ritonavir™, macrolide antibiotics and oil soluble anesthetics such as Propofol™ are also useful in this invention. The synthetic and natural forms of steroidal hormones such as estrogens, estradiols, progesterone, testosterone, cortisone, phytoestrogens, dehydroepiandrosterone (DHEA), growth hormones and the like can also be used in this invention. Also useful in the present invention are the oil soluble acids and alcohols such as tartaric acid, lactylic acid, butylated hydroxyanisole, butylated hydroxytoluene, lignin, sterols, polyphenolic compounds, oryzanol, cholesterol, lignin, phytosterols, flavonoids such as quercetin and reservatol, diallyl disulfides and the like. Polar lipids such as the phospholipids and ether lipids can also be used. Oil soluble vitamins including the synthetic and natural forms of vitamin A, E, D and K, carotenoids and lycopenes can also be used in this invention.

The present invention also contemplates the use of the structured glycerides in a nutritionally complete food product or a nutritional supplement containing a lipophilic compound whose absorption is desired to be enhanced. The food product or supplement may comprise the fat composition of the invention, additional oils, an amino nitrogen source such as protein, protein hydrolysates or elemental amino acids, a carbohydrate source and appropriate levels of the oil soluble vitamins, nutrients and/or drugs. The product may be in a ready-to-feed liquid form, or in the form of a powder or concentrated liquid adapted to provide a ready-to-feed product by the addition of water and stirring.

In addition to nutritional formulation, the composition according to the invention may be formulated as a tablet, pill, capsule, suppository, spray, lozenge, ear drops, eye drops or topical formula for application to the skin (i.e. lotions, ointments, trans-dermal patches and the like). The structured glyceride component and lipophilic compound(s) may also be microencapsulated or in the form of liposomes.

The lipophilic compounds useful in the present invention can be at concentrations from a few parts per million to 90% by wt, including any interim concentrations, as is appropriate for delivering the particular lipophilic compound. When in the form of a dietary supplement or pharmaceutical preparation, the structured glyceride and lipophilic compound may comprise from 10–100 wt. % of the dietary supplement or pharmaceutical preparation. An enteral formula utilizing the present invention will typically contain from 1–20% by wt. of the structured glyceride component/lipophilic compound. Those skilled in the art of preparation of enteral formulas will be readily able to determine what sources of amino nitrogen, carbohydrates, vitamins and minerals would be suitable for combination with the structured triglyceride/lipophilic compound physical mixture of the present invention.

Process of Making

The structured glycerides of this invention may be prepared by any procedure commonly used to make structured lipids. For example, an interesterification or transesterification reaction made by mixing oils, or selective fractions of the oils, in stoichiometric proportions and then causing the transesterification reaction to proceed using catalysts or enzymes could be used. In addition, one skilled in the art could genetically engineer the oil bearing plants to produce the specific structured glycerides described in this invention. Although a standard transesterfication procedure may result in a component mixture containing the structured glycerides of the invention along with other oils, such a component mixture is intended to be included within the claims.

It is possible to source MCT oils as starting materials to prepare the structured lipids useful in this invention. MCT oils, such as fractionated coconut oil and fractionated palm kernel oils, are obtained by the hydrolysis of coconut and palm kernel oils and the distillation of the fatty acids. The fatty acids are then re-esterified to the glycerol molecules to obtain the MCT oil.

The chemical interesterification process used for the preparation of the structured triglycerides in the following examples is according to the teachings found in the "Oils and Fats Manual, A Comprehensive Treatise", Vol. 2, Chapter 11, *Transformation of Fat for Use in Food Products*, pgs. 923–925, the entire teaching of which is hereby incorporated by reference. Chemical interesterification, also called co-randomization (since it alters the non-random distribution of nature) may be accomplished by heating a mixture of oils for a short period of time (e.g. from 0.5 to 4 hours, preferably 0.5 to 2 hours at temperatures of 100–140° C., preferably 110–130° C.) in the presence of a catalyst such as sodium methylate or sodium methoxide (e.g. range from 0.05 to 0.5% by wt., more preferably from 0.1 to 0.3% by wt.) The fatty acids leave their natural position on the triglyceride and rearrange in a random fashion (presumably equally on each of the three positions). Thus, about one third of each individual fatty acid will re-esterify at the sn-1 position, about one third on sn-2 and about one third on sn-3.

The examples below describe the distribution resulting from the co-randomization of equal weight parts of an MCT oil (having medium chain fatty acids, "MCFA" or M) and a fish oil (having long chain polyunsaturated fatty acids, "LCPUFA" or L) in addition to the distribution resulting from the co-randomization with twice as much MCFA as LCPUFA. Of course, other ratios of MCFA to LCPUFA are within the invention, including from about 1:3 to about 3:1, more typically from about 1:2 to about 2:1. The distribution of triglyceride entities that result from these combinatorial probabilities can be represented as follows with the approximate yields shown:

TABLE 1

STRUCTURED TRIGLYCERIDE PROBABILITY OF OCCURRENCE

| Triglyceride | Probability of Occurrence 1:1 MCFA and LCPUFA mix | | |
|---|---|---|---|
| MLM | $(1/2)^3 = 1/8$ | (12.5%) | |
| LMM | $(1/2)^3 = 1/8$ | (12.5%) | |
| MML | $(1/2)^3 = 1/8$ | (12.5%) | |
| Total 2 MCFA, 1 LCPUFA yield | | | 37.5% |
| LML | $(1/2)^3 = 1/8$ | (12.5%) | |
| LLM | $(1/2)^3 = 1/8$ | (12.5%) | |
| MLL | $(1/2)^3 = 1/8$ | (12.5%) | |
| Total 1 MCFA, 2 LCPUFA yield | | | 37.5% |
| Subtotal | | | 75% |
| LLL | $(1/2)^3 = 1/8$ | | 12.5% |
| MMM | $(1/2)^3 = 1/8$ | | 12.5% |
| Total | | | 100% |

| Triglyceride | Probability of Occurrence 2:1 MCFA and LCPUFA mix | | |
|---|---|---|---|
| MLM | $(2/3)^2(1/3) = 4/27$ | (14.8%) | |
| LMM | $(1/3)(2/3)^2 = 4/27$ | (14.8%) | |
| MML | $(2/3)^2(1/3) = 4/27$ | (14.8%) | |
| Total 2 MCFA, 1 LCPUFA yield | | | 44.4% |
| LML | $(1/3)^2(2/3) = 2/27$ | (7.4%) | |
| LLM | $(1/3)^2(2/3) = 2/27$ | (7.4%) | |
| $(2/3)(1/3)^2 = 2/27$ | (7.4%) | | |
| Total 1 MCFA, 2 LCPUFA yield | | | 22.2% |
| Subtotal | | | 66.6% |
| LLL | $(1/3)^3 = 1/27$ | | 3.7% |
| MMM | $(2/3)^3 = 8/27$ | | 29.6% |
| Total | | | 99.9% |

New, non-natural triglycerides are created in the random re-esterification of the MCFA and the LCPUFA as shown in Table 1. An exemplary co-randomized structured triglyceride made according to this process is described in Example 1, below. As described above, altering the ratio of MCT oil (MCFA) to fish oil (LCFA) will alter the yield percentages in mathematically predictable ways. The formula for the probability of occurrence of a specific triglyceride is $P=(3,n)(pl^n)(pm^{(3-n)})$ where pl is the probability of occurrence of L, pm is the probability of occurrence of M, n is the number of Ls in the triglyceride and (3,n) is the total number of ways n objects can be selected from 3 objects. For any triglyceride the combinatorial expression (3,n) resolves to one of the following: (3,1)=3, (3,2)=3 and (3,3)=1. Therefore, the probability of occurrence of a triglyceride with twice as much MCFA as LCPUFA is $(3,1)(1/3)^1(2/3)^{3-1}=12/27$ or 44.4%, the sum of the probabilities of occurrence of the entities: MML, MLM, LMM (see Table 1).

An important difference between the structured triglyceride component and a physical mix of its constituent oils is found in the molecular species of the triglycerides. The individual molecular species of the structured glyceride component are designated by the Equivalent Carbon Number (ECN). The interesterification (or co-randomization) of the constituent oils creates new triglyceride species which are unique and are absent in the constituent oils. Specifically, the described co-randomization process produces triglyceride species having ECN about 32 to 42 that are simply not found in physical mixtures of the constituent oils. Structured glyceride components of this invention will preferably contain at least 40% by weight of ECN greater than 30 to less than 48 species. More preferably, the structured glyceride component will contain at least 60% by weight of the ECN greater than 30 to less than 48, most preferably at least 60% by weight of the ECN of about 32 to about 42 species.

Without being bound to any theory or mechanism, the inventors believe that these differences, in part, are responsible for the structured lipid's ability to enhance the absorption and transport of lipophilic compounds into the lymphatic system as compared to the physical blend of oils.

The following Examples are intended to illustrate the present invention, not limit it. Rather, the invention is defined by the appended claims.

EXAMPLE 1

Part A. Physical mixture: Equal weights of MCT oil (Stepan, Inc. of New Jersey, USA) and fish oil (Mochida, Ltd. of Tokyo, Japan) were blended and mixed well to comprise the "physical mix" experimental oil.

Part B. Structured Triglyceride: Equal weights of MCT oil (Stepan, Inc. of New Jersey, USA) and fish oil (Mochida, Ltd. of Tokyo, Japan) were co-randomized according to the teachings found in "Oils and Fats Manual, A Comprehensive Treatise", Vol 2, Chapter 11, *Transformation of Fat for Use in Food Products*, pgs. 923–925 using sodium methoxide as the catalyst, to manufacture the "structured triglyceride component" experimental oil.

The fatty acid composition of the structured triglyceride component of Part B and the physical mixture of Part A is set forth in Table 2. As seen in Table 2, below, the fatty acid compositions of the two experimental oils are essentially identical.

TABLE 2

FATTY ACID COMPOSITION OF EXPERIMENTAL OILS

| Fatty Acid | MCT Oil Weight % | Fish Oil Weight % | Physical Mix Weight % | Structured Triglyceride Weight % |
|---|---|---|---|---|
| 8:0 | 55.7 | — | 27.6 | 27.0 |
| 10:0 | 43.4 | — | 20.7 | 20.5 |
| 12:0 | 0.8 | 0.3 | 0.5 | 0.5 |
| 14:0 | 0.1 | 5.9 | 3.0 | 2.9 |
| 16:0 | — | 9.5 | 4.9 | 4.7 |
| 16:1n-7 | — | 8.3 | 4.2 | 4.1 |
| 18:0 | — | 1.2 | 0.6 | 0.6 |
| 18:1n-9 | — | 11.7 | 6.0 | 5.7 |
| 18:2n-6 | — | 1.7 | 0.9 | 0.8 |
| 18:4n-3 | — | 2.8 | 1.5 | 1.5 |
| 20:1n-9 | — | 1.9 | 1.0 | 1.0 |
| 20:4n-6 | — | 2.8 | 1.5 | 1.5 |
| 20:5n-3 | — | 28.7 | 14.7 | 15.1 |
| 22:5n-3 | — | 3.2 | 1.7 | 1.8 |
| 22:6n-3 | — | 13.1 | 6.8 | 8.0 |
| Others | — | 8.9 | 4.4 | 4.3 |
| Total | 100.0 | 100.0 | 100.0 | 100.0 |

Table 3 sets forth the ECN species profile of the two experimental oils of parts A and B, above.

TABLE 3

TRIGLYCERIDE PROFILE OF EXPERIMENTAL OILS

| Sample ID ECN* | Physical Mix % Weight | Structured Triglycerides % Weight |
|---|---|---|
| 24 | 11.5 | 4.3 |
| 26 | 21.8 | 8.3 |
| 28 | 14.4 | 5.7 |
| 30 | 3.4 | 2.8 |
| 32 | 0.0 | 5.9 |
| 34 | 0.0 | 8.8 |
| 35 | 0.0 | 10.8 |
| 37 | 0.0 | 11.2 |
| 38 | 0.0 | 5.4 |
| 39 | 0.0 | 2.4 |
| 41 | 0.0 | 5.2 |
| 42 | 0.0 | 6.0 |
| 44 | 0.5 | 6.0 |
| 46 | 1.8 | 5.1 |
| 47 | 0.0 | 4.0 |
| 48 | 4.1 | 0.0 |
| 49 | 0.0 | 1.6 |
| 50 | 7.3 | 1.3 |
| 52 | 8.7 | 1.5 |
| 53 | 9.0 | 1.3 |
| 55 | 7.7 | 1.1 |
| 57 | 5.4 | 0.7 |
| 58 | 2.4 | 0.0 |
| 59 | 0.4 | 0.8 |
| 60 | 1.7 | 0.0 |
| Total | 100.0 | 100.0 |
| Sum-ENC 32–47 | 0 | 70.8 |

*ECN: Equivalent carbon number.

It can be seen that the species of ECN 32 to 47 are absent or nearly absent in the physical mix oil; yet these species comprise 70.8% by weight of the structured triglyceride oil. Furthermore, greater than half (55.7%) of the triglyceride oil are species of ECN 32 to 42 and are these are completely nonexistent in the physical mixture. The co-randomization process has clearly created new chemical species.

EXAMPLE 2

This experiment was conducted to determine if a structured glyceride consisting of a co-randomized MCT/fish oil would enhance the absorption of lipophilic compounds such as vitamin E (tocopherol) and retinol (vitamin A) using a lymph fistula rat model based upon a procedure described by Fujimoto et al., "Effect of Ischemia-Reperfusion on Lipid Digestion and Absorption in Rat Intestine", Am. J. Physiol., 260: G595–G602 (1991), the entire teaching of which is hereby incorporated by reference. This model was designed to represent fat absorption mode of the healthy intestinal tract (i.e., not compromised through disease or ischemic event). The lymph fistula rat model is extremely accurate in measuring and quantitating lipid absorption.

The physical mix (Part A) and structured triglyceride component (Part B) of Example 1 were used. Radiolabeled retinol and α-tocopherol used in this Example and in Example 3 are commercially available from Hoffman-LaRoche, Inc. (New Jersey, USA).

Male Sprague Dawley rats weighing between 280 and 330 grams were all fed a normal Purina Rat Chow for one week. Rats were fasted overnight prior to surgery and under anesthesia, a laparotomy was performed, the intestinal lymph duct was cannulated according to the procedure of Tso et al., "The Absorption of Lipid and Lipoprotein Synthesis", Lipid Research Methodology, Chapter 5: 191–216 (1984) Alan R. Liss, Inc., N.Y., N.Y, the entire teaching of which is hereby incorporated by reference. The superior mesenteric artery was isolated but not occluded as in the injury model used in Example 3. A silicon infusion tube (1.6 mm OD) was placed in the stomach for infusion of saline, structured lipid/lipophilic compound or emulsified physical mix/lipophilic compound. The fundic incision was closed by a purse string suture. The animals were allowed to recover for 24 hours before experimental oil/lipophilic compound infusion began.

Animals were randomly assigned to two groups in this non-injury model. Animals were intragastrically infused 24 hours after surgery with 1.0 ml of MCT/fish oil structured glyceride (Example I, Part B) for Group B or 1.0 ml of its equivalent physical mixture (Example I, Part A) for Group A. Radiolabeled tocopherol and retinol (lipophilic compounds) were added to the structured triglyceride component and to the physical mix. 90 mM of tocopherol was administered to each animal in combination with 1 mCi of $^{14}$C-tocopherol. 0.528 mM of retinol was administered to each animal in combination with 10 mCi of $^3$H-retinol.

Lymph was collected in pre-cooled tubes beginning hourly for eight (8) hours after initiation of lipid infusion. At the end of the lipid infusion, the animals were sacrificed by exsanguination.

Radioactivity was measured in an aqueous miscible scintillant (Poly-Fluor, Packard, Downers Grove, Ill.). Samples were counted for 10 minutes in a liquid scintillation spectrophotometer (LKB Model 1209, Pharmacia, Inc.). Samples were corrected for quenching by reference to a series of $^{14}$C and $^3$H standards that were progressively quenched.

Lymph lipids were extracted and the methyl ester derivatives of the fatty acids were analyzed using a Hewlett Packard Gas Chromatograph, Model 5890A with a capillary column packed with 10% SP-2330 on 80/100 Supelcoport (Supelco, Inc., Bellefonte, Pa.).

The lymphatic retinol absorption measured in $\mu$mol per hour is presented in FIG. 1. FIG. 1 demonstrates that the structured triglyceride component according to this invention increased the lymphatic absorption of retinol over the entire 8 hour study period. In similar fashion, FIG. 2 demonstrates that the structured glyceride component according to this invention enhances the lymphatic absorption of tocopherol over the entire 8 hour study period. This experiment clearly demonstrates that the use of a structured triglyceride, in accordance with the invention, in combination with a lipophilic compound, such as vitamins A and E, can result in at least a 30% higher (p<0.01) lymph output of the lipophilic compound compared to the corresponding physical mix in this normal absorption model. It is important to note that the lymph tocopherol and retinol increased rapidly and maintained a significantly higher output (p<0.01) with the structured glyceride component versus the physical mix.

EXAMPLE 3
Ischemia/Reperfusion Injury Model

This experiment was conducted in a manner similar to Example 2 except that the ischemic/reperfusion injury model was used. This model was used to simulate the lipid malabsorption conditions associated with diseases such as Short Bowel Syndrome, Crohn's disease and the like. Animals were divided into two groups and given the physical mix (Group A) or the structured triglyceride component (Group B) of Example 2. The major difference in this experiment was that the superior mesenteric artery was occluded for 25 minutes with a clamp and at the end of that ischemic period the clamp was released with a few drops of lidocaine which was applied directly onto the artery to facilitate reperfusion.

Figure 3:
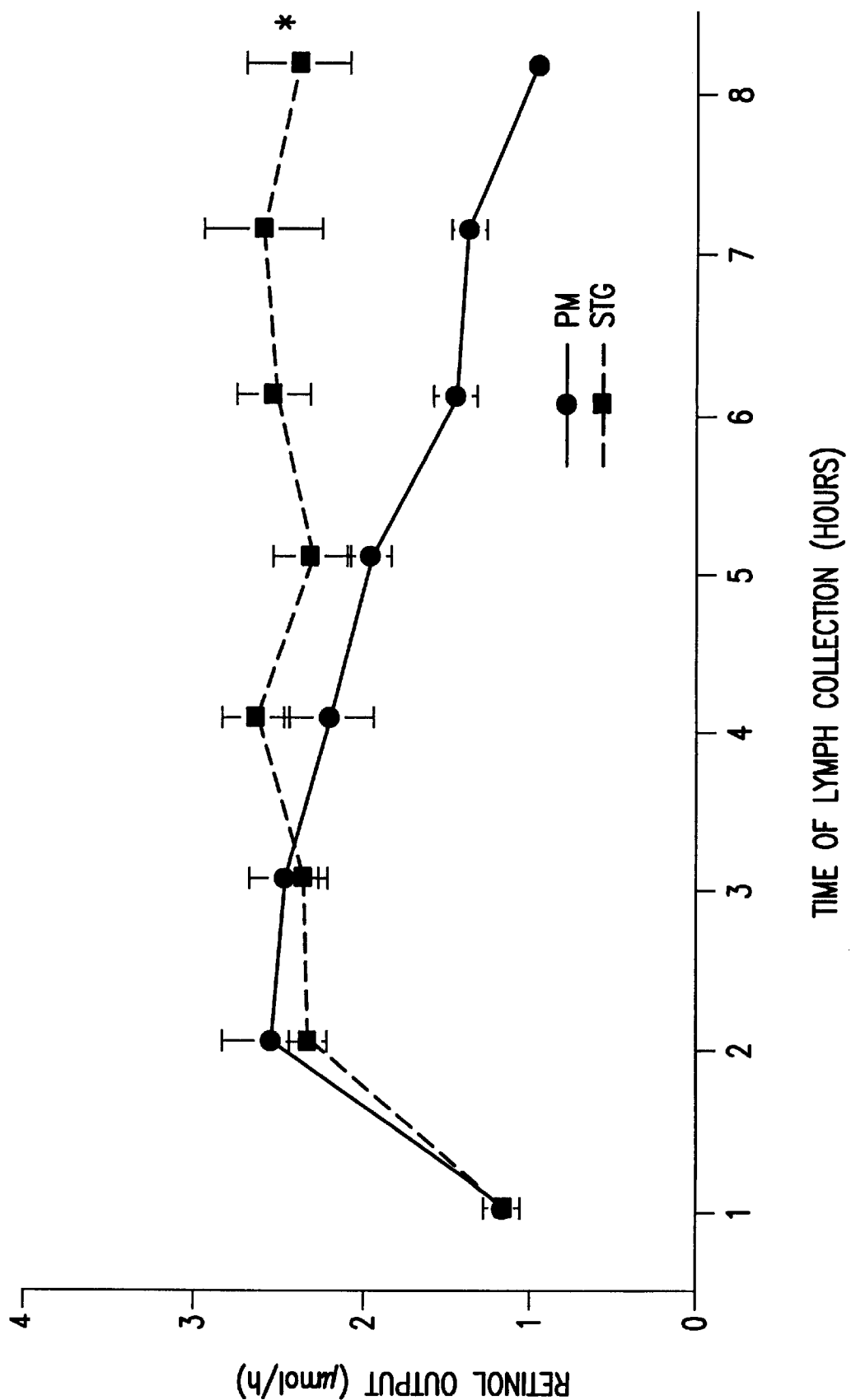
FIG. 3 is a graphic representation of lymphatic retinol absorption for the ischemia/reperfusion injury model experiment conducted in Example 3.

FIG. 3 graphically represents the lymphatic retinol absorption over the 8 hour study period. The data represents that over the initial 3 hour period, the lymphatic absorption of retinol was about equal between the structured triglyceride component and the physical mixture.

However, after about 3 hours, the structured triglyceride component evidences an enhancement in the retinol absorption over the physical mix. At the end of the 8 hour study, the structured triglyceride component was providing more than twice the amount of retinol to the lymphatic circulation than the physical mixture.

Figure 4:
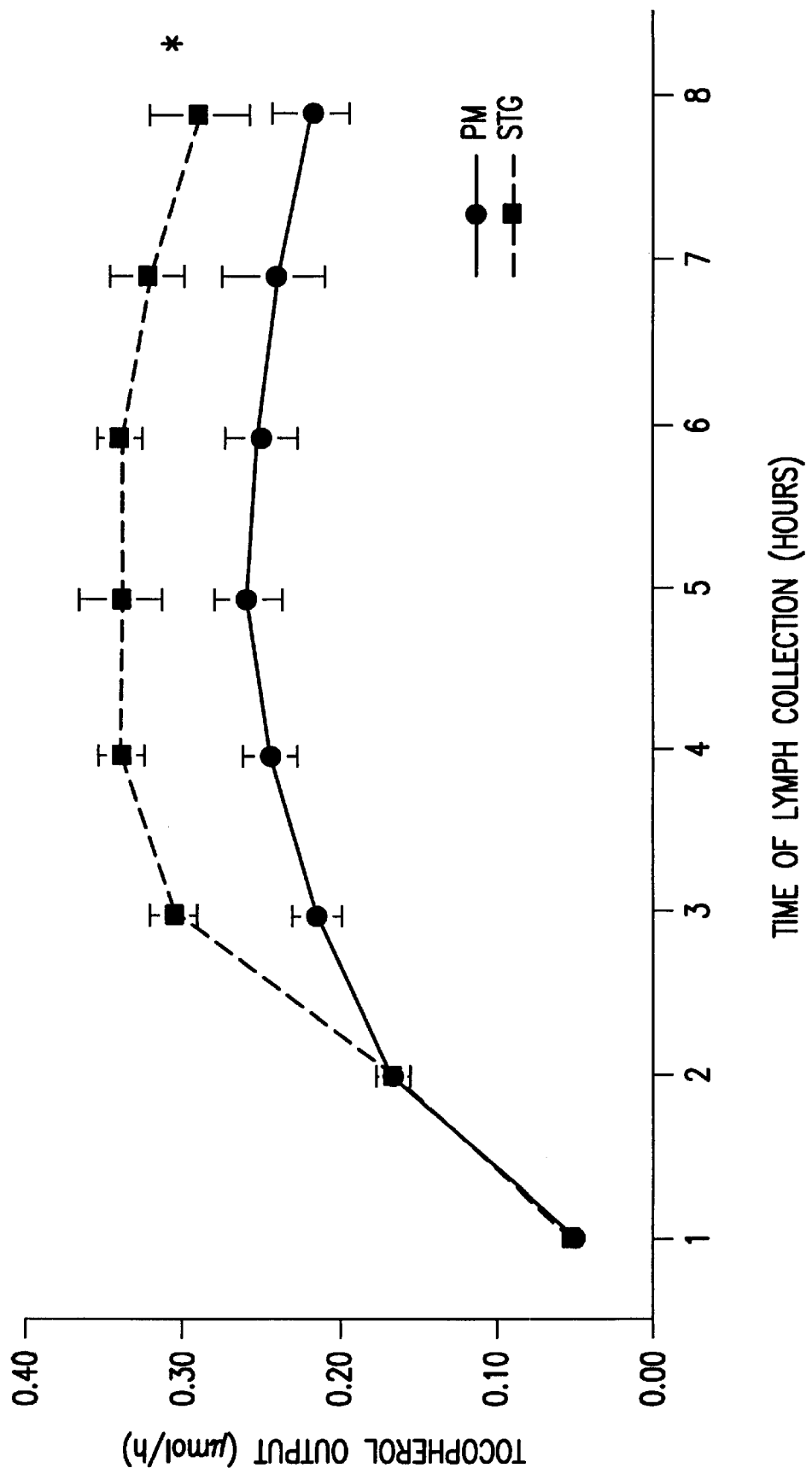
FIG. 4 is the graphic representation of lymphatic tocopherol absorption for the ischemia/reperfusion injury model experiment conducted in Example 3.
Figure 5:
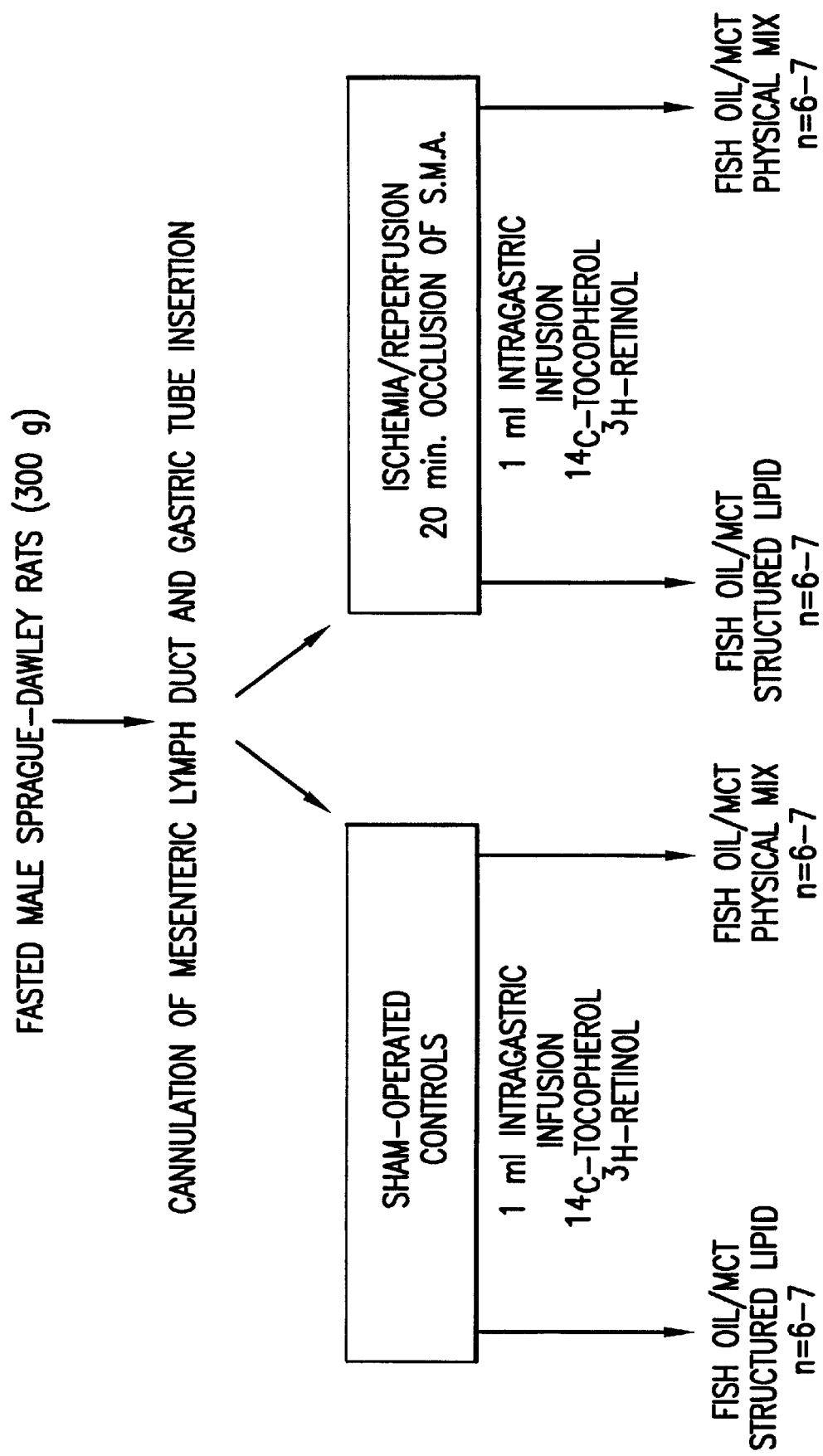
FIG. 5 describes the study design with a flow diagram for Examples 2 and 3.

FIG. 4 represents the data collected regarding the absorption of tocopherol. In similar fashion, the initial 2 hour period of tocopherol absorption was essentially equal between the structured triglyceride component and the physical mix, however, after about 2 hours, the structured triglyceride showed a significantly enhanced level of lymphatic tocopherol absorption. This experiment clearly demonstrates that the structured triglyceride component can result in at least a 30% ($p<0.01$) higher lymph output of the lipophilic compound to the corresponding physical mix in the malabsorptive rat model.

Industrial Applicability

The medical community continues to seek methods to overcome the problems associated with the administration of oil soluble drugs, nutrients and vitamins. The need to provide adequate absorption of these lipophilic compounds to patients with malabsorptive diseases such as Crohn's disease or Short bowel disease, present special problems. The novel method of this invention which comprises the administration of a structured glyceride in conjunction with a lipophilic compound such as vitamins A and E, oil soluble drugs and nutrients, fulfills this long felt need. The method of the present invention can be accomplished through the administration of pills, capsules, suppositories, lozenges, transdermal patches, sprays, drops, dietary supplements, pharmaceutical preparations and the like that utilize the structured glyceride/lipophilic compound physical mixture described herein.

Modifications and alternative embodiments of the invention will be apparent to those skilled in the art in view of the foregoing description. Accordingly, this description is to be construed as illustrative only and is for the purpose of teaching those of skill in the art the manner of carrying it out.

We claim:

1. A method for enhancing an animal's absorption of at least one lipophilic compound, said method comprising administering to said animal:
   (a) at least one lipophilic compound in conjunction with;
   (b) a structured glyceride component characterized in that it contains some triglyceride species and at least 40% of the triglyceride species have:
      (i) about 33 to 70 wt. % of medium chain acyl moieties having 4 to 12 carbon atoms;
      (ii) about 30 to 67 wt. % of long chain acyl moieties having more than 12 carbon atoms; and
      (iii) an equivalent carbon number of greater than 30 to less than 48.

2. The method according to claim 1 wherein said structured glyceride component predominantly comprises triglycerides.

3. The method according to claim 2 wherein said triglycerides comprise 45 to 65 wt. % of acyl moieties having 4 to 12 carbon atoms.

4. The method according to claim 2 wherein said triglycerides comprise 35 to 55 wt. % of acyl moieties having more than 12 carbon atoms.

5. The method according to 2 wherein said triglycerides comprise 45 to 65 wt. % of acyl moieties having 4 to 12 carbon atoms and 35 to 55 wt. % of acyl moieties having more than 12 carbon atoms.

6. A method according to claim 5 in which at least 60% by weight of said structured glyceride has an equivalent carbon number of about 32 to about 42.

7. A method according to claim 2 in which said structured glyceride has an equivalent carbon number of about 32 to about 42.

8. The method according to claim 1 wherein said lipophilic compound is selected from the group consisting of oil soluble drugs, nutrients and vitamins.

9. The method according to claim 8 wherein said lipophilic compound is a vitamin selected from the group consisting of vitamin A and vitamin E.

10. A method according to claim 8 in which said oil soluble drug selected from the group consisting of immunosuppressive agents, protease inhibitors, macrolide antibiotics, anesthetics, estrogens, estradiols, progesterone, testosterone, cortisone, phytoestrogens, dehydroepiandrosterone, and growth hormone.

11. A method according to claim 8 in which said vitamins are selected from the group consisting of vitamin A, vitamin E, vitamin D, vitamin K, carotenoids, and lycopenes.

12. The method according to claim 1 wherein the structured glyceride component is prepared by interesterification of an oil containing predominantly medium chain triglycerides and an oil containing predominantly long chain triglycerides in a ratio from about 1:2 to about 2:1.

13. The method of claim 12 wherein said structured glyceride component is prepared by chemical interesterification.

14. A method according to claim 12 in which said lipophilic compound is an oil soluble drug selected from the group consisting of immunosuppressive agents, protease inhibitors, macrolide antibiotics, anesthetics, estrogens, estradiols, progesterone, testosterone, cortisone, phytoestrogens, dehydroepiandrosterone, and growth hormone.

15. A method according to claim 12 in which said lipophilic compound is a vitamin selected from the group consisting of vitamin A, vitamin E, vitamin D, vitamin K, carotenoids, and lycopenes.

16. A method according to claim 12 in which said medium chain triglycrides are obtained from fractionated coconut oil, fractionated palm kernel oil, or a mixture thereof.

17. A method according to claim 12 in which said long chain triglycerides are obtained from an oil selected from the group consisting of borage, black currant seed, corn, coconut, canola, soybean, marine oils, fungal oils, safflower, high oleic safflower, sunflower, high oleic sunflower, olive, evening primrose, cottonseed, rice bran, grapeseed, flaxseed, butterfat, garlic, peanuts, almonds, walnuts, wheat germ, egg, sesame, lard, tallow and mutton.

18. The method according to claim 1 wherein at least 40% of the triglyceride species have an equivalent carbon number of about 32 to about 42.

19. The method according to claim 1 wherein said animal suffers from a lipid malabsorption condition.

20. A method according to claim 1 in which said medium chain acyl moieties have from 6 to 12 carbon atoms.

21. A method according to claim 1 in which said medium chain acyl moieties have from 8 to 10 carbon atoms.

22. A method according to claim 1 in which said structured glyceride has an equivalent carbon number of about 32 to about 42.

23. A composition comprising:
(a) at least one lipophilic compound; and
(b) a structured glyceride component characterized in that it contains some triglyceride species and at least 40% of the triglyceride species have:
   (i) about 33 to 70 wt. % of acyl moieties having 4 to 12 carbon atoms;
   (ii) about 30 to 67 wt. % of acyl moieties having more than 12 carbon atoms; and
   (iii) an equivalent carbon number of greater than 30 to less than 48.

24. The composition according to claim 23 wherein said structured glyceride component predominantly comprises triglycerides.

25. The composition according to claim 24 wherein said triglycerides comprise 45 to 65 wt. % of acyl moieties having 4 to 12 carbon atoms.

26. The composition according to claim 24 wherein said triglycerides comprise 35 to 55 wt. % of acyl moieties having more than 12 carbon atoms.

27. The composition according to claim 24 wherein said triglycerides comprise 45 to 65 wt. % of acyl moieties having 4 to 12 carbon atoms and 35 to 55 wt. % of acyl moieties having more than 12 carbon atoms.

28. A composition according to claim 27 in which said at least 60% by weight of said structured glyceride has an equivalent carbon number of about 32 to about 42.

29. A composition according to claim 24 in which said structured glyceride has an equivalent carbon number of about 32 to about 42.

30. The composition according to claim 23 wherein the structured glyceride component is prepared by interesterification of an oil containing predominantly medium chain triglycerides and an oil containing predominantly long chain triglycerides in a ratio from about 1:2 to about 2:1.

31. The composition according to claim 30 wherein said structured glyceride is prepared by chemical interesterification.

32. A composition according to claim 30 in which said lipophilic compound is an oil soluble drug selected from the group consisting of immunosuppressive agents, protease inhibitors, macrolide antibiotics, anesthetics, estrogens, estradiols, progesterone, testosterone, cortisone, phytoestrogens, dehydroepiandrosterone, and growth hormone.

33. A composition according to claim 30 in which said lipophilic compound is a vitamin selected from the group consisting of vitamin A, vitamin E, vitamin D, vitamin K, carotenoids, and lycopenes.

34. A composition according to claim 30 in which said medium chain triglycrides are obtained from fractionated coconut oil, fractionated palm kernel oil, or a mixture thereof.

35. A composition according to claim 30 in which said long chain triglycerides are obtained from an oil selected from the group consisting of borage, black currant seed, corn, coconut, canola, soybean, marine oils, fish oils, fungal oils, safflower, high oleic safflower, sunflower, high oleic sunflower, olive, evening primrose, cottonseed, rice bran, grapeseed, flaxseed, butterfat, garlic, peanuts, almonds, walnuts, wheat germ, egg, sesame, lard, tallow and mutton.

36. A composition according to claim 30 in which said long chain triglycerides are obtained from fish oil.

37. A composition according to claim 36 in which said medium chain triglycerides are obtained from fractionated coconut oil.

38. The composition according to claim 23 wherein said lipophilic compound is selected from the group consisting of oil soluble drugs, nutrients and vitamins.

39. The composition according to claim 38 wherein said lipophilic compound is a vitamin selected from the group consisting of vitamin A and vitamin E.

40. The composition according to claim 23 wherein at least 40% of the triglyceride species have an equivalent carbon number of about 32 to about 42.

41. A composition according to claim 23 in which said oil soluble drug is selected from the group consisting of immunosuppressive agents, protease inhibitors, macrolide antibiotics, anesthetics, estrogens, estradiols, progesterone, testosterone, cortisone, phytoestrogens, dehydroepiandrosterone, and growth hormone.

42. A composition according to claim 23 in which said vitamins are selected from the group consisting of vitamin A, vitamin E, vitamin D, vitamin K, carotenoids, and lycopenes.

43. A composition according to claim 23 in which said medium chain acyl moieties have from 6 to 12 carbon atoms.

44. A composition according to claim 23 in which said medium chain acyl moieties have from 8 to 10 carbon atoms.

45. A composition according to claim 23 in which said structured glyceride has an equivalent carbon number of about 32 to about 42.

46. A composition according to claim 23 in which said structured glyceride component contains at least 90% by weight triglycerides.

47. A composition according to claim 23 in which said structured glyceride component contains at least 60% by weight triglycerides which have an equivalent carbon number of about 32 to about 42.

* * * * *